(12) United States Patent
Li et al.

(10) Patent No.: US 6,639,401 B2
(45) Date of Patent: Oct. 28, 2003

(54) CONTACTLESS, TRANSFORMER-BASED MEASUREMENT OF THE RESISTIVITY OF MATERIALS

(75) Inventors: Zongjin Li, Clear Water Bay (HK); Wenlai Li, Clear Water Bay (HK)

(73) Assignee: The Hong Kong University of Science and Technology, Hong Kong (HK)

( * ) Notice: Subject to any disclaimer, the term of this patent is extended or adjusted under 35 U.S.C. 154(b) by 0 days.

(21) Appl. No.: 09/907,817

(22) Filed: Jul. 19, 2001

(65) Prior Publication Data

US 2003/0016009 A1 Jan. 23, 2003

(51) Int. Cl.[7] .................. G01N 27/72; G01R 27/08; G01R 33/12
(52) U.S. Cl. .................. 324/239; 324/228; 324/693; 324/713
(58) Field of Search .................. 324/201, 211, 324/227, 228, 239–243, 445, 545, 117 R, 691, 693, 696, 704, 705, 713, 724, 654, 656

(56) References Cited

U.S. PATENT DOCUMENTS

| | | | |
|---|---|---|---|
| 2,829,338 A | * 4/1958 | Lord | 324/211 X |
| 3,068,380 A | * 12/1962 | Lamoreaux | 324/211 X |
| 3,867,688 A | * 2/1975 | Koski | 324/445 |
| 3,925,724 A | * 12/1975 | Steingroever | 324/243 |
| 4,449,095 A | * 5/1984 | Steingroever et al. | 324/223 |
| 4,634,462 A | * 1/1987 | Fish et al. | 65/29.18 |
| 5,008,621 A | * 4/1991 | Jiles | 324/227 |
| 5,105,146 A | * 4/1992 | Wolf | 324/117 R |
| 5,446,383 A | * 8/1995 | Pearse et al. | 324/239 X |
| 5,793,214 A | * 8/1998 | Wakamatsu | 324/445 X |
| 5,855,721 A | * 1/1999 | Monteiro et al. | 324/240 X |
| 6,100,685 A | * 8/2000 | Kim et al. | 324/223 |
| 6,366,076 B1 | * 4/2002 | Karrer et al. | 324/117 R |

* cited by examiner

Primary Examiner—Gerard R. Strecker
(74) Attorney, Agent, or Firm—Burns, Doane, Swecker & Mathis, L.L.P.

(57) ABSTRACT

The present invention provides an apparatus and method for measuring the resistivity of a sample of cement-based material. A transformer is formed with a primary coil, a secondary formed by means of a sample of said cement-based material, means for supplying a voltage to said primary, means for measuring the voltage induced in said sample, and means for measuring the current induced in said sample. The resistance of the sample can be measured and thus the resistivity of the concrete sample can be calculated.

11 Claims, 3 Drawing Sheets

CONTACTLESS, TRANSFORMER-BASED MEASUREMENT OF THE RESISTIVITY OF MATERIALS

FIELD OF THE INVENTION

This invention relates to an apparatus and method for the measurement of the resistivity of concrete and cement-based materials having improved accuracy and repeatability in comparison with conventional technologies.

BACKGROUND OF THE INVENTION

Concrete and similar cement-based materials are widely used in the construction and building industries because they are highly versatile low-cost building materials. In many applications it is necessary or desirable to measure the electrical resistivity of concrete or other cement-based materials.

Such measurements may be carried out, for example, in determining the physical properties and characteristics of such materials, especially with regard to monitoring how such properties change with the age of the material. In addition, in many situations concrete and cement-based materials may be used in the manufacture of buildings and rooms used for the research, manufacture and storage or the like of electrical components, and semi-conductor products. In many such cases it is desirable to form an electrically shielded room and if concrete or a like cement-based material is the primary construction material, then it is necessary to be able to determine the resistivity of the concrete or the like.

PRIOR ART

Conventionally, the resistivity of a concrete or cement-based material is determined by forming a specimen of the material in the form of a prism, and then measuring the current and voltage between two plate electrodes placed against opposing sides of the specimen. It will be readily apparent that in such conventional methods of resistivity measurement, the contact between the plate electrodes and the sample is of the greatest importance. If the contact is loose, inaccurate and sometimes nonsensical measurements will be obtained.

In order to improve the contact fresh cement paste or colloidal graphite can be placed between the sides of the specimen and the electrodes. Also, an external force can be used to clamp the electrodes firmly to the sides of the sample. These techniques, however, are only effective at the beginning of measurements, as hydration of the sample will cause shrinkage leading to the formation of cracks and fissures in the sample that eventually mean that the measurements can no longer be made with any reliability at all. Furthermore when a cement paste is used to improve the connection, because the paste is highly alkaline it corrodes the electrodes which thus have to be replaced at very regular intervals.

In summary there exists no completely satisfactory method of obtaining reliable, and repeatable measurements of the resistivity of a concrete or cement-based material.

SUMMARY OF THE INVENTION

According to the present invention there is provided apparatus for measuring the resistivity of a sample of cement-based material, comprising: a transformer formed with a primary coil, a secondary coil formed by means of a sample of said cement-based material, means for supplying a voltage to said primary coil, means for measuring the voltage induced in said sample, and means for measuring the current induced in said sample.

In a first embodiment the transformer is a double arm transformer and the primary and secondary are both formed around a transformer core.

In a second embodiment the transformer is a single arm transformer and the primary is wound around a transformer core and the secondary is formed around said single arm.

Preferably the sample is formed as a ring of said cement-based material. The ring may be annular, or may be rectangular.

Preferably the voltage measuring means comprises a coil formed on a surface of the ring and extending circumferentially around said sample. Preferably the current measuring means surrounds a radial section of said sample. The current sensing means may be a leakage current meter, or may be a Rogowski coil.

Viewed from another aspect the present invention provides a method for measuring the resistivity of a sample of cement-based material, comprising:

(a) forming a sample of said material as a secondary of a transformer, (b) applying a voltage to a primary of said transformer, (c) measuring the voltage induced in said sample, (d) measuring the current induced in said sample, and (e) determining the resistively of said sample from the results of steps (c) and (d).

BRIEF DESCRIPTION OF THE DRAWINGS

Some embodiments of the invention will now be described by way of example and with reference to the accompanying drawings, in which.

DETAILED DESCRIPTION OF PREFERRED EMBODIMENTS

The present invention overcomes or at least mitigates the problems with the prior art by providing an apparatus and method for determining the electrical resistivity of a concrete or cement-based material that does not require the use of electrodes in contact with a sample, but instead uses a contactless transformer-based method in which a specimen of the material is formed so as to form a secondary coil of the transformer.

Figure 1:
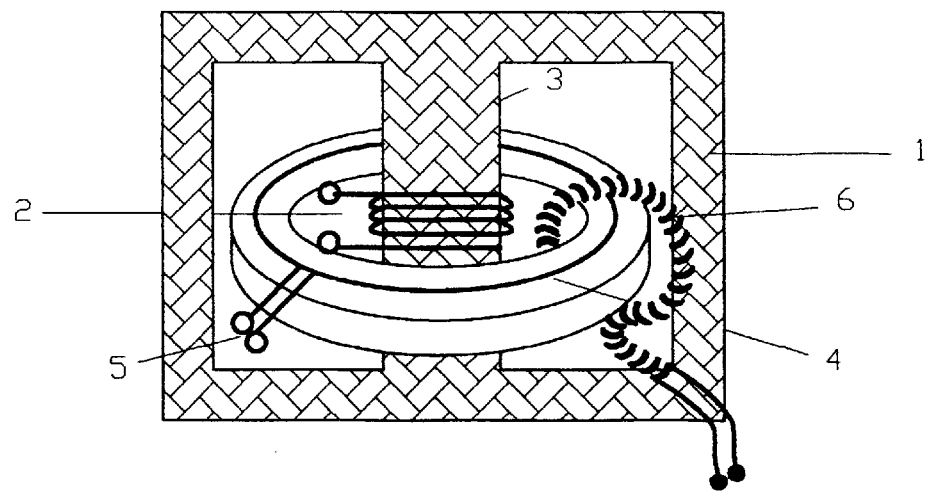
FIG. 1 is a schematic view of a first embodiment of the invention.

FIG. 1 shows a first embodiment of the invention. In this embodiment a double arm transformer core 1 is provided, and a primary coil 2 is wound round the core 3 of the transformer. In this embodiment of the invention, the secondary of the transformer is formed by a sample 4 of the concrete or cement-based material to be measured. The sample 4 is a molded ring of the concrete or cement-based material. The sample 4 may be an annular ring as shown in FIG. 1, or it may be a rectangular ring which could be easier to mould. A single coil 5 is formed on an upper surface of the sample 4 to enable toroidal voltage measurement. A Rogowski coil or leakage current meter is provided surrounding a section of the sample to measure the current flowing in the sample.

Figure 2:
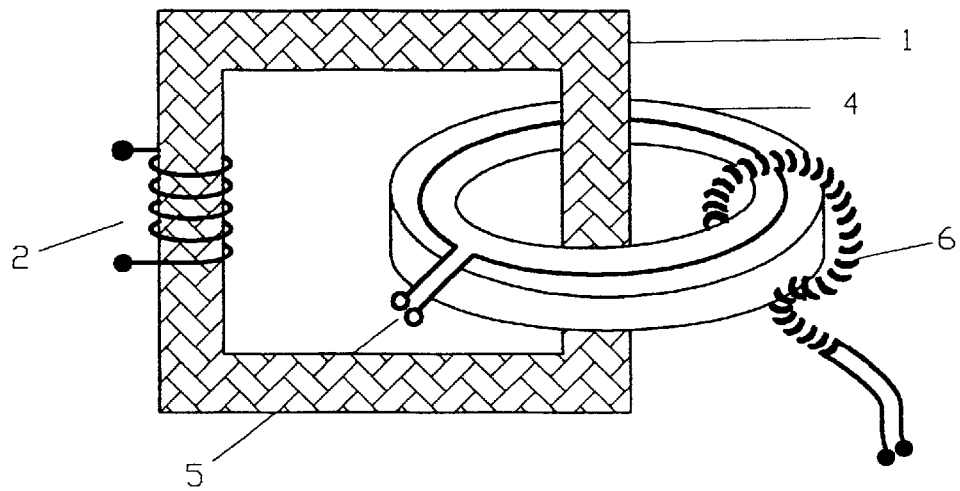
FIG. 2 is a schematic view of a second embodiment of the invention.

FIG. 2 shows an alternate embodiment in which the transformer is of a single arm type. The primary coil is wound around the transformer core, while a sample of the material to be measured is formed as a ring surrounding the single arm.

In use of the embodiments of the invention, an AC voltage is applied to the primary coil and as a consequence a toroidal voltage (V) is induced in the secondary, ie in the sample of concrete or cement-based material. By measurement of this toroidal voltage and the induced current flowing in the sample, the impedance and resistivity of the sample can be determined as will be explained in the following example where the sample is an annular ring, and with reference to FIG. 3 which is the equivalent electrical circuit, and FIG. 4 which shows a sample of material in section.

The current induced in the sample is dependent on the radius r of the sample and the current distribution has a gradient along the diameter of the sample that is proportional to 1/r. By using a Rogowski coil or like leakage current meter surrounding the complete cross-section of the secondary, the current is integrated and the measured result (I) is not dependent on the exact position of the sample forming the secondary or the point at which the current is measured.

Figure 3:
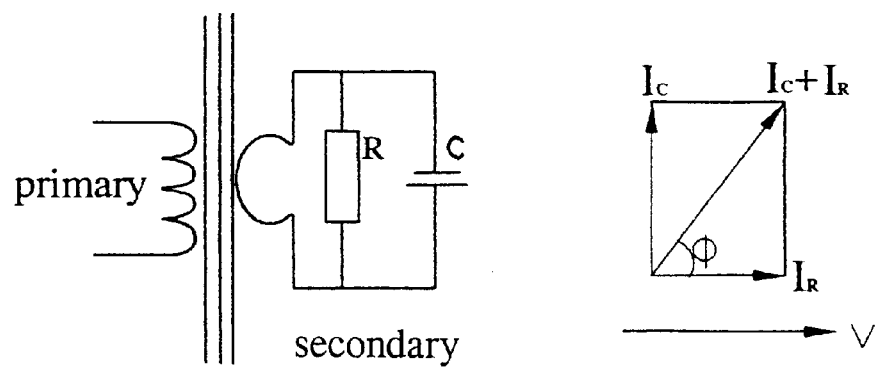
FIG. 3 illustrates the equivalent circuit.
Figure 4:
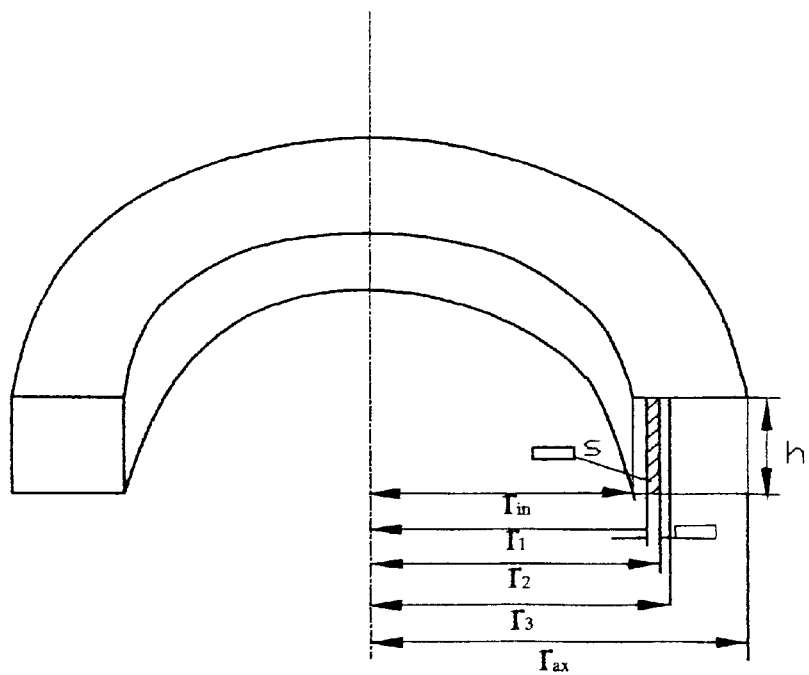
FIG. 4 illustrates in section a concrete specimen.

Because of the physical characteristics of concrete and cement-based materials, they are not pure resistors and the equivalent circuit is shown as FIG. 3 in which R is resistance of the sample, C is the capacitance of the sample.

The resistivity of the concrete sample may be calculated from the equation:

$$\rho = Rh.ln(r_{ex}/r_{in})/2\pi$$

where h is the height of the ring specimen, $r_{ex}$ is the external radius and $r_{in}$, is the internal radius, and R is calculated by the equation:

$$R = V_{p\text{-}p}/(I_{p\text{-}p} \cos \phi)$$

Where $V_{p\text{-}p}$ is the toroidal voltage (peak to peak), $I_{p\text{-}p}$ is the current flowing in the specimen (peak to peak) and $\phi$ is the phase difference between the toroidal voltage and the current. The phase difference can be measured during the measurements, and in practice it is found to be close to zero. In theory the resistivity may be frequency dependent, but in a range of around 1 MHz to 2 MHz the resistivity may be regarded as frequency independent. 2 MHZ may therefore be chosen as a suitable measurement frequency.

Figure 5:
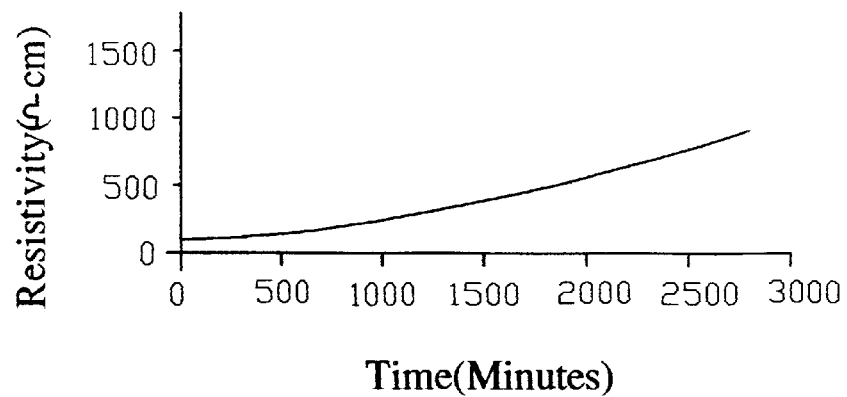
FIG. 5 is a graph showing the results for three samples of identically formed concrete.
Figure 6:
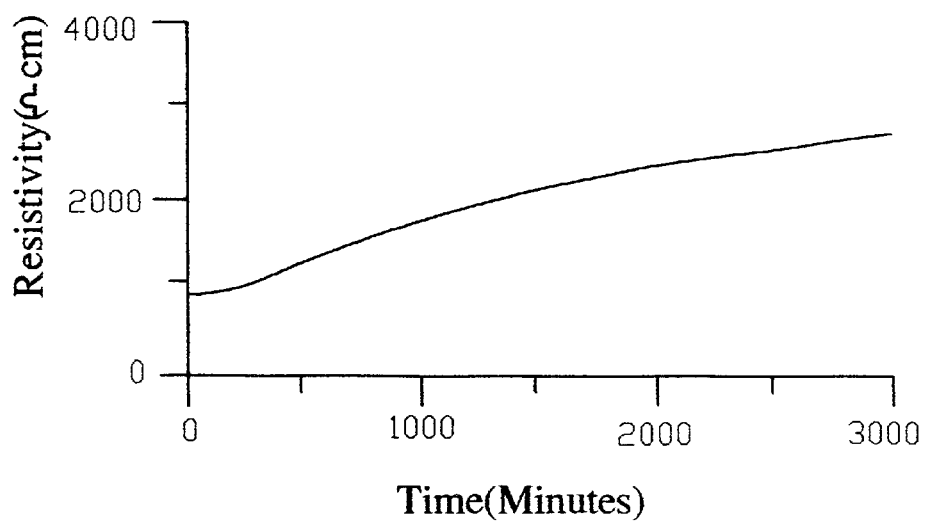
FIG. 6 is a graph showing the measured resistivity of a sample using a traditional method.

FIG. 5 plots the resistivity against time for three identically formed samples made of Portland Type I cement and water (with a water cement ratio of 0.5). The similarity of the three curves shows that the measurement method of the present invention has very good repeatability characteristics. In contrast to FIG. 5, FIG. 6 plots the resistivity against time for a very similar sample of concrete using a traditional method with electrodes. It will be seen that the traditional method produces higher values for the resistivity, probably as a consequence of the contact between the sample and the electrode. Furthermore using the traditional method there is a greater increase of the measured resistivity against time.

What is claimed is:

1. Apparatus for measuring the resistivity of a sample of material, comprising: a transformer formed with a primary coil, a secondary formed by a sample of said material that is inductively coupled to said primary coil, means for supplying a voltage to said primary, means for measuring the voltage induced in said sample, and means for measuring the current induced in said sample.

2. Apparatus as claimed in claim 1 wherein said transformer includes a core having a leg about which said primary and said secondary are both formed.

3. Apparatus as claimed in claim 1 wherein said transformer includes a core having a first leg about which said primary is wound and a second leg around which said secondary is formed.

4. Apparatus as claimed in claim 1 wherein said sample is formed as a ring of cement-based material.

5. Apparatus as claimed in claim 4 wherein said ring is annular.

6. Apparatus as claimed in claim 4 wherein said ring is rectangular.

7. Apparatus as claimed in claim 4 wherein said voltage measuring means comprises a coil formed adjacent a surface of said ring and extending circumferentially around said sample.

8. Apparatus as claimed in claim 4 wherein said current measuring means surrounds a radial section of said sample.

9. Apparatus as claimed in claim 8 wherein said current sensing means is a leakage current meter.

10. Apparatus as claimed in claim 8 wherein said current sensing means is a Rogowski coil.

11. A method for measuring the resistivity of a sample of material, comprising:
   (a) forming a sample of said material as a secondary of a transformer,
   (b) applying a voltage to a primary of said transformer,
   (c) measuring the voltage induced in said sample,
   (d) measuring the current induced in said sample, and
   (e) determining the resistivity of said sample from the results of steps (c) and (d).

* * * * *